(12) United States Patent
Hayam et al.

(10) Patent No.: US 8,359,092 B2
(45) Date of Patent: Jan. 22, 2013

(54) DETERMINING LOCATIONS OF GANGLIA AND PLEXI IN THE HEART USING COMPLEX FRACTIONATED ATRIAL ELECTROGRAM

(75) Inventors: Gal Hayam, Tivon (IL); Warren Jackman, Oklahoma City, OK (US); Hiroshi Nakagawa, Edmond, OK (US)

(73) Assignee: Biosense Webster, Inc., Diamond Bar, CA (US)

( * ) Notice: Subject to any disclaimer, the term of this patent is extended or adjusted under 35 U.S.C. 154(b) by 403 days.

(21) Appl. No.: 12/275,380

(22) Filed: Nov. 21, 2008

(65) Prior Publication Data

US 2009/0192393 A1 Jul. 30, 2009

Related U.S. Application Data

(60) Provisional application No. 60/990,961, filed on Nov. 29, 2007.

(51) Int. Cl.
*A61B 5/04* (2006.01)

(52) U.S. Cl. .................................. 600/523; 600/509

(58) Field of Classification Search .......... 600/508–510, 600/515–518, 522–523
See application file for complete search history.

(56) References Cited

U.S. PATENT DOCUMENTS

| | | | |
|---|---|---|---|
| 5,483,968 A * | 1/1996 | Adam et al. | 600/508 |
| 5,546,951 A | 8/1996 | Ben-Haim | |
| 5,738,096 A | 4/1998 | Ben-Haim | |
| 6,226,542 B1 | 5/2001 | Reisfeld | |
| 6,301,496 B1 | 10/2001 | Reisfeld | |
| 6,332,089 B1 | 12/2001 | Acker et al. | |
| 6,345,203 B1 * | 2/2002 | Mueller et al. | 607/60 |
| 6,618,612 B1 | 9/2003 | Acker et al. | |
| 6,669,692 B1 | 12/2003 | Nelson et al. | |
| 6,690,963 B2 | 2/2004 | Ben-Haim et al. | |
| 6,892,091 B1 | 5/2005 | Ben-Haim et al. | |
| 7,289,843 B2 * | 10/2007 | Beatty et al. | 600/513 |
| 2003/0120150 A1 | 6/2003 | Govari | |
| 2004/0068178 A1 | 4/2004 | Govari | |
| 2004/0102769 A1 | 5/2004 | Schwartz et al. | |
| 2004/0147920 A1 | 7/2004 | Keidar | |
| 2005/0099290 A1 | 5/2005 | Govari | |
| 2007/0197929 A1 * | 8/2007 | Porath et al. | 600/523 |

(Continued)

FOREIGN PATENT DOCUMENTS

| | | |
|---|---|---|
| EP | 1808124 A | 7/2007 |
| WO | WO 96/05768 | 2/1996 |

OTHER PUBLICATIONS

Nakagawa; Heart Rhythem Elsevier, vol. 4 No. 5; Apr. 6, 2007 p. S73;—Effective Localization of Left Atrial Autonomic Ganglionated Plexi Using a Computer Algorithm During Mapping in Atrial Fibrillation.

(Continued)

*Primary Examiner* — Niketa Patel
*Assistant Examiner* — Catherine Voorhees
(74) *Attorney, Agent, or Firm* — Louis J. Capezzuto (57) ABSTRACT

Software and apparatus are provided to automatically detect and map ganglionated plexi that are found within areas of complex fractionated electrograms in cardiac chambers. Electrogram signal are analyzed to count the number of complexes whose amplitude and peak-to-peak intervals meet certain criteria. Functional maps indicating a spatial distribution of the ganglionated plexi and the relative numbers of complex fractionated electrograms are produced for display.

12 Claims, 4 Drawing Sheets

U.S. PATENT DOCUMENTS

2007/0208260 A1    9/2007    Afonso
2008/0009758 A1*   1/2008    Voth .............................. 600/523

OTHER PUBLICATIONS

Lemery; Heart Rhythm, Elsevier, vol. 3, No. 4, Apr. 1, 2006; pp. 387-396—Feasibility study of endocardial mapping of ganglionated plexuses during catheter abilation of atrial fibrillation.

Jiaxiong; J. Cardiovascular Electrophysiology.; Nov. 2007; vol. 18, No. 11—Autonomic mechanism to explain complex fractionated atrial electrograms.

Hou, Yinglong et al. Ganglionated Plexi Modulate Extrinsic Cardiac Autonomic Nerve Input: Effects on Sinus Rate, Atrioventricular Conduction, Refractoriness, and Inducibility of Atrial Fibrillation, J. Am. Coll. Cardiol. 2007;50;61-68.

Nademanee, Koonlawee, M.D. Facc et al. A New Approach for Catheter Ablation of Atrial Fibrillation: Mapping of the Electrophysiologic Substrate, J. Am. Coll. Cardiol. 2004;43;2044-2053.

Biosense Webster, Inc., Inventors: Joshua Porath et al. filed on Jan. 5, 2007 as U.S. Appl. No. 11/620,370—pending.

* cited by examiner

DETERMINING LOCATIONS OF GANGLIA AND PLEXI IN THE HEART USING COMPLEX FRACTIONATED ATRIAL ELECTROGRAM

CROSS-REFERENCE TO RELATED APPLICATIONS

This Application claims the benefit of U.S. Provisional Application No. 60/990,961, entitled "Determining Locations of Ganglia Plexus (GP) Areas in the Heart Using CFAE", filed Nov. 29, 2007, which is herein incorporated by reference. This Application shares disclosure with copending application Ser. No. 11/620,370, entitled "Mapping of Complex Fractionated Atrial Electrogram", filed 5 Jan. 2007.

BACKGROUND OF THE INVENTION

1. Field of the Invention

This invention relates to the diagnosis and treatment of cardiac arrhythmias. More particularly, this invention relates to the mapping of ganglionated neural plexi in the heart that are associated with arrhythmogenic areas.

2. Description of the Related Art

The meanings of certain acronyms and abbreviations used herein are given in Table 1.

TABLE 1

| Acronyms and Abbreviations | |
|---|---|
| GP | Ganglionated Plexi |
| AF | Atrial Fibrillation |
| CFAE | Complex Fractionated Atrial Electrogram |

Cardiac arrhythmias such as atrial fibrillation are an important cause of morbidity and death. Commonly assigned U.S. Pat. No. 5,546,951, and U.S. Pat. No. 6,690,963, both issued to Ben Haim; and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. No. 6,226,542, and U.S. Pat. No. 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multipleelectrode catheters have been developed to simultaneously measure electrical activity at multiple points in the heart chamber.

Over the past decade, several mapping studies in human atrial fibrillation have made the following important observations. Atrial electrograms during sustained atrial fibrillation have three distinct patterns: single potential, double potential and a complex fractionated atrial electrograms (CFAE's). The CFAE areas represent the atrial fibrillation substrate sites and become important target sites for ablation. By ablating areas having persistent CFAE's, atrial fibrillation may be eliminated and even rendered non-inducible.

In the document *Ganglionated Plexi Modulate Extrinsic Cardiac Autonomic Nerve Input*, Hou et al., Journal of the American College of Cardiology Vol. 50, No. 1, 2007, it is suggested that ablation of the four left atrial autonomic ganglionated plexi (GP) can improve success of ablation procedures for the treatment of atrial fibrillation. The authors used high frequency stimulation to locate the ganglionated plexi for this purpose. High frequency stimulation, however, is cumbersome and time consuming, requiring special equipment and skills.

SUMMARY OF THE INVENTION

An embodiment of the invention provides a method for mapping abnormal electrical activity in a heart of a living subject, which is carried out by obtaining electrical signal data from respective locations of the heart, automatically analyzing the signal data to identify complex fractionated electrograms therein, identifying one or more of the locations as having ganglionated plexi responsively to presence of complex fractionated electrograms at the one or more of the locations, deriving an electroanatomic map of the heart from the signal data that includes a spatial distribution of the complex fractionated electrograms and the ganglionated plexi, and displaying the electroanatomic map.

According to an aspect of the method, identifying one or more of the locations includes determining that a number of the complex fractionated electrograms at the one or more of the locations complies with a predefined criterion.

According to a further aspect of the method, compliance with the predefined criterion includes identifying at least a threshold number of the complex fractionated electrograms at a location.

According to still another aspect of the method, compliance with the predefined criterion includes identifying ones of the locations having locally maximal numbers of complex fractionated electrograms.

Another aspect of the method is carried out by electrically stimulating selected locations that presumptively contain ganglionated plexi, and then recording a cardiovascular response including at least one of: a reduction in sinus rate, a reduction in blood pressure, and a period of asystole, and thereafter reporting a confirmation of a presence of the ganglionated plexi in the selected locations.

According to one aspect of the method, deriving an electroanatomic map includes coding the electroanatomic map according to numbers of the complex fractionated electrograms detected in the respective locations.

Other embodiments of the invention provide computer software product and apparatus for carrying out the above-described method.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known tangible media for use with a data processing system, such as a diskette, hard drive, or CD-ROM. The code may be distributed on such media, or may be distributed to users from the memory or storage of one computer system over a network of some type to storage devices on other computer systems for use by users of such other systems.
System Architecture.

Figure 1:
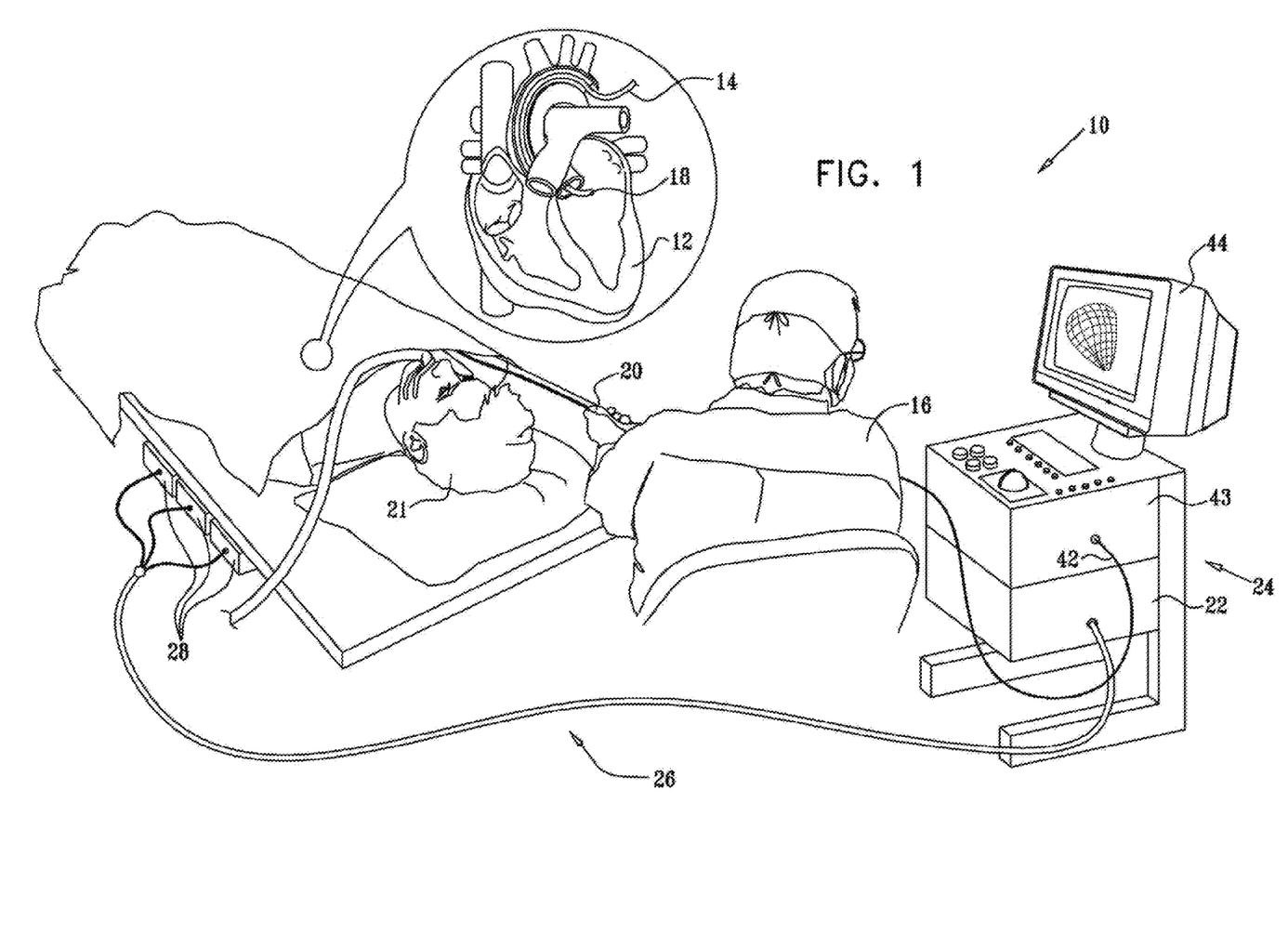
FIG. 1 is a pictorial illustration of a system for detecting areas of abnormal electrical activity and performing ablative procedures on a heart of a living subject in accordance with a disclosed embodiment of the invention.

Turning now to the drawings, reference is initially made to FIG. 1, which is a pictorial illustration of a system 10 for detecting areas of abnormal electrical activity and performing ablative procedures on a heart 12 of a living subject 21 in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

Areas determined to be abnormal by evaluation of the electrical activation maps can be ablated application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention are disclosed with respect to atrial complex fractionated electrograms, but can be applied to all heart chambers, to epicardial as well as endocardial approaches, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14 may be adapted, mutatis mutandis, from the ablation catheter described in commonly assigned U.S. Pat. No. 6,669,692, whose disclosure is herein incorporated by reference. The console 24 typically contains an ablation power generator 43.

The positioning processor 22 is an element of a positioning subsystem 26 that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning subsystem 26 comprises a magnetic position tracking system that determines the position and orientation of the catheter 14. The positioning subsystem 26 generates magnetic fields in a predefined working volume its vicinity and senses these fields at the catheter. The positioning subsystem 26 typically comprises a set of external radiators, such as field generating coils 28, which are located in fixed, known positions external to the patient. The coils 28 generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking systems that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning subsystem 26 shown in FIG. 1 uses magnetic fields, the methods described below may be implemented using any other suitable positioning subsystem, such as systems based on electromagnetic fields, acoustic or ultrasonic measurements.

Figure 2:
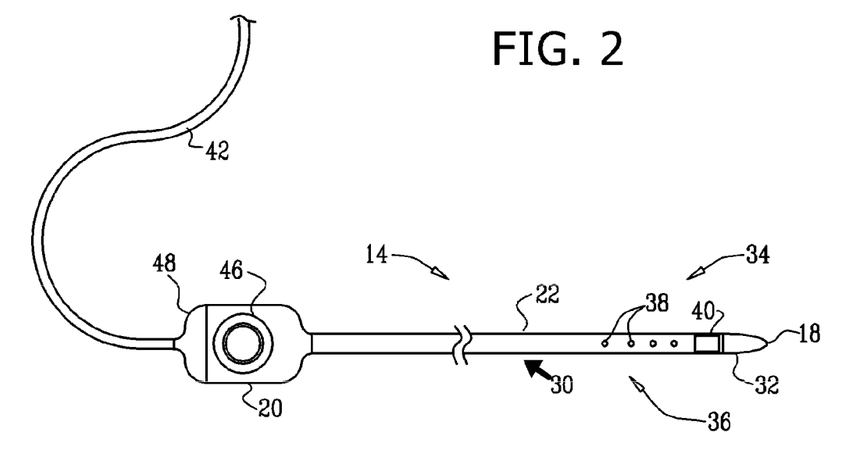
FIG. 2 is a diagram of an embodiment of a catheter for use in the system shown in FIG. 1.

Reference is now made to FIG. 2, which is a diagram of an embodiment of the catheter 14 for use in the system 10 (FIG. 1). The catheter 14 is a mapping and therapeutic delivery catheter for insertion into the human body, and into a chamber of the heart 12 (FIG. 1). The catheter shown is exemplary; many other types of catheters can be used as the catheter 14. The catheter 14 includes a body 30. An electrode 32 is at a distal portion 34 disposed for measuring the electrical properties of the heart tissue. The electrode 32 is also useful for sending electrical signals to the heart for diagnostic purposes, e.g., for electrical mapping, and/or for therapeutic purposes, e.g., for ablating defective cardiac tissue. The distal portion 34 further includes an array 36 of non-contact electrodes 38 for measuring far field electrical signals in the heart chamber. The array 36 is a linear array in that the non-contact electrodes 38 are linearly arranged along the longitudinal axis of the distal portion 34. The distal portion 34 further includes at least one position sensor 40 that generates signals used to determine the position and orientation of the distal tip 18 within the body. The position sensor 40 is preferably adjacent to the distal tip 18. There is a fixed positional and orientational relationship of the position sensor 40, the distal tip 18 and the electrode 32.

The position sensor 40 transmits, in response to the fields produced by the positioning subsystem 26 (FIG. 1), position-related electrical signals over a cable 42 running through the catheter 14 to the console 24. Alternatively, the position sensor 40 in the catheter 14 may transmit signals to the console 24 over a wireless link, as described in U.S. Patent Application Publication Nos. 2003/0120150 and 2005/0099290, the disclosures of which are herein incorporated by reference. The positioning processor 22 then calculates the location and orientation of the distal portion 34 of the catheter 14 based on the signals sent by the position sensor 40. The positioning processor 22 typically receives, amplifies, filters, digitizes, and otherwise processes signals from the catheter 14. The positioning processor 22 also provides a signal output to a display 44 that provides a visual indication of the position of the distal portion 34 and/or the distal tip 18 of the catheter 14 relative to the site chosen for ablation.

The handle 20 of the catheter 14 includes controls 46 to steer or deflect the distal portion 34, or to orient it as desired.

The cable 42 comprises a receptacle 48, which connects to the handle 20. The receptacle 48 is preferably configured to receive catheters of a specific model, and preferably includes user-evident identification of the specific model. One of the advantages in using the cable 42 is the ability to connect different models and types of catheters, such as those catheters having different handle configurations, to the same console 24 (FIG. 1). Another advantage in having a separate cable 42 is in the fact that it does not come into contact with patients, so that it is possible to reuse the cable 42 without sterilization. The cable 42 further contains one or more isolation transformers (not shown), which electrically isolate the catheter 14 from the console 24. The isolation transformers may be contained in the receptacle 48. Alternatively, isolation transformers may be contained in the system electronics of the console 24.

Referring again to FIG. 1, the system 10 can be realized as the CARTO XP EP Navigation and Ablation System, available from Biosense Webster, Inc., 3333 Diamond Canyon Road, Diamond Bar, Calif. 91765, and suitably modified to execute the procedures described herein.

Electrical Mapping.

Figure 3:
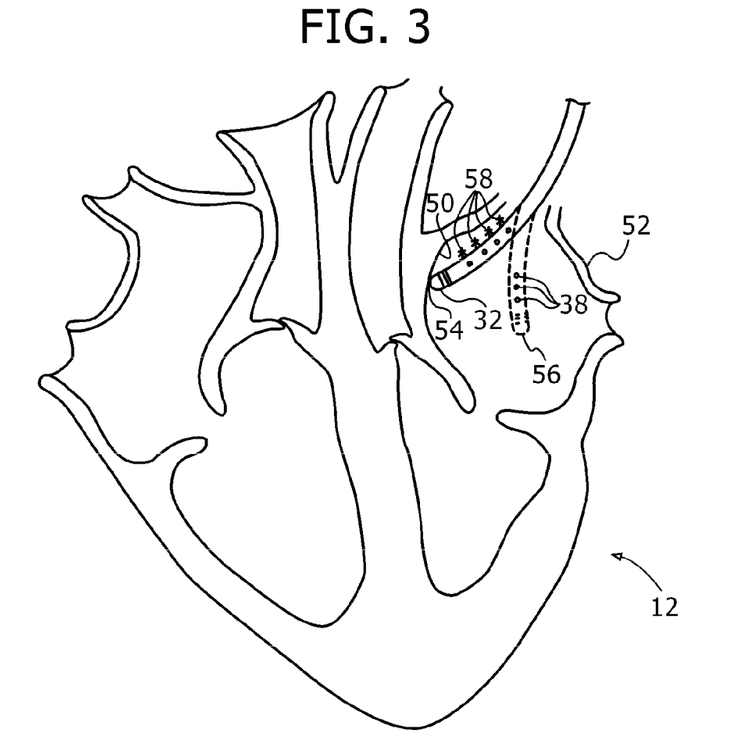
FIG. 3 is a diagram depicting the distal end of a catheter in contact with the endocardial surface of the right atrium of a heart, in accordance with a disclosed embodiment of the invention.

Using the system 10 (FIG. 1), an electrical activation map of a chamber of the heart 12 can be generated using the methods described in the above-noted U.S. Pat. No. 6,892,091. A summary of one of these methods, modified according to the aspects of the present invention, will facilitate an understanding of the invention. Reference is now made to FIG. 3, which depicts the distal end of the catheter 14 in contact with an endocardial surface 50 of the right atrium 52 of the heart 12, in accordance with a disclosed embodiment of the invention. The electrode 32 is maintained in contact with the endocardial surface 50 at a current contact point 54 throughout at least an entire cardiac cycle. During this time, location information is continuously measured by the position sensor 40 (FIG. 2), while electrical information, preferably, voltage (as a function of time), is measured by the electrode 32 and each of the non-contact electrodes 38 in the array 36 (FIG. 2).

After the above electrical and location information is collected at the contact point 54, the electrode 32 is contacted with another contact point, e.g., a contact point 56 elsewhere on the endocardial surface of the right atrium 52. Points 58, shown as asterisks, represent the locations of the non-contact electrodes 38 while the electrode 32 was in contact with the contact point 54.

The electrode 32 is advanced over a plurality of contact points on the cardiac chamber's endocardial surface. Location and electrical information is acquired while the contact electrode is in contact with each of the contact points. Typically, the above-described contacting and information acquisition steps are effected at between 5-15 such contact points. Since there are multiple non-contact electrodes 38, the total number of points used to acquire data in a chamber may be 160 points or more. The resultant location and electrical information acquired from the electrode 32 and the non-contact electrodes 38 at each of acquisition step provides the basis for generating an electrical map of the heart chamber.

The location of the contact electrodes at each of the contact points may be used to define the geometric map of the cardiac chamber. While not actually contacting the cardiac surface, the totality of the non-contact electrode locations defines a "cloud" of space, which represents a minimum chamber volume. These non-contact locations may be used, alternatively, or together with the location of the electrode 32 at each of the contact points, to define the chamber geometry.

It is preferable to use a reference location sensor to correct for patient movement during the procedure or to movement of the heart due to patient breathing. One method of obtaining a location reference is by the use of a reference catheter (not shown) containing a reference location sensor elsewhere in the heart. Alternatively, a reference location sensor may be contained in a pad that might be attached external to the patient, for example on the back of the patient. In either case, locations determined by the sensors contained in the mapping catheter may be corrected for patient movement with the reference sensors.

A preferred method for generating the electrical map of the heart from the acquired location and electrical information is described in the above noted U.S. Pat. No. 6,226,542. Briefly, an initial, generally arbitrary, closed 3-dimensional curved surface (also referred to herein for brevity as a curve) is defined in a reconstruction space in the volume of the sampled points. The closed curve is roughly adjusted to a shape, which resembles a reconstruction of the sampled points. Thereafter, a flexible matching stage is preferably repeatedly performed one or more times in order to bring the closed curve to accurately resemble the shape of the actual volume being reconstructed. The 3-dimensional surface may be rendered to a video display or other screen for viewing by a physician or other user of the map.

The initial closed curved surface preferably encompasses substantially all the sampled points or is interior to substantially all the sampled points. However, it is noted that any curve in the vicinity of the sampled points is suitable. Preferably, the closed three-dimensional curved surface comprises an ellipsoid, or any other simple closed curve. Alternatively, a non-closed curve may be used, for example, when it is desired to reconstruct a single wall rather than the entire volume.

A grid of a desired density is defined on the curve. For each of the points on the grid, a vector is defined, which is dependent on the displacement between one or more of the grid points and one or more of the measured locations on the cardiac surface. The surface is adjusted by moving each of the grid points in response to the respective vector, so that the reconstructed surface is deformed to resemble the actual configuration of the cardiac chamber. The grid preferably divides the curved surface into quadrilaterals or any other polygons such that the grid evenly defines points on the curve. Preferably, the grid density is sufficient such that there are generally more grid points than sampled points in any arbitrary vicinity. Further preferably, the grid density is adjustable according to a desired compromise between reconstruction accuracy and speed.

CFAE Identification.

Automatic detection of CFAE's is described in detail in the above-noted copending application Ser. No. 11/620,370. However, a brief discussion here will facilitate understanding of some aspects of the present invention. CFAE's are nominally defined as areas that exhibit one of the following characteristics. In practice, a user or operator may vary these characteristics according to his experience and judgment with respect to a particular patient:

(1) areas of the atrium that have fractionated electrograms composed of two deflections or more and/or perturbation of the baseline with a continuous deflection of a prolonged activation complex over a 10-sec recording period; or (2) areas of the atrium where the electrogram has a very short cycle length (e.g., 120 ms) averaged over a 10 second recording period. The recording period is not critical, and recording intervals of other lengths may be used.

In aspects of the current embodiment the number of intervals between complexes is represented. However, this not limiting, and other types of information derived from data manipulation may form a basis for representing the number and characteristics of complexes.

In order to identify CFAE's, fractionated complex duration mapping tools were constructed as a modification of the system software of the above-noted CARTO XP EP Navigation and Ablation System. Although the software is described with reference to this particular system, the invention is not limited to the CARTO XP EP Navigation and Ablation System, but can be applied to many other electrical mapping systems by those skilled in the art.

The following parameters were used to produce functional electro-anatomic maps of the heart, optimized to show areas of CFAE.

1. ICL (Interval Confidence Level) map with 10-40 color scale.
2. Minimum voltage threshold 0.04 mV.
3. Maximum voltage threshold 0.2 mV.
4. Minimum duration 15 ms.
5. Maximum duration 80 ms.

Identification of Ganglionated Plexi.

The normal locations of ganglionated plexi in the heart are known; however there is anatomic variability among subjects. Moreover, areas of the heart containing the ganglionated plexi are characterized by continuous or intermittent CFAE's. If the number of CFAE's in an area of interest exceeds a predetermined threshold, typically 40, in one approach, ganglionated plexi are presumptively identified. Alternatively, ganglionated plexi may be considered to exist in areas of interest having locally maximal numbers of CFAE segments, irrespective of the actual number of CFAE's.

Optionally, although identification of ganglionated plexi using CFAE mapping as described above, the existence of such ganglionated plexi can be confirmed by applying high-frequency electrical stimulation to areas presumptively containing ganglionated plexi, using a bipolar electrode probe. Stimulation at 20 Hz, 12 volts, with a pulse width of 10 ms is suitable. If such areas indeed are sites of ganglionated plexi, the response to the stimulation should be one or more of the following cardiovascular effects, which mimic vagal stimulation: reduction in blood pressure; reduction in sinus rate; or asystole lasting for a few cycles. Any of these responses is considered to confirm the presence of ganglionated plexi at the current site of stimulation. If the effects are not observed, then it is concluded that ganglionated plexi are not confirmed to be present.

Electrical Mapping of Ganglionated Plexi and CFAE's.

Figure 4:
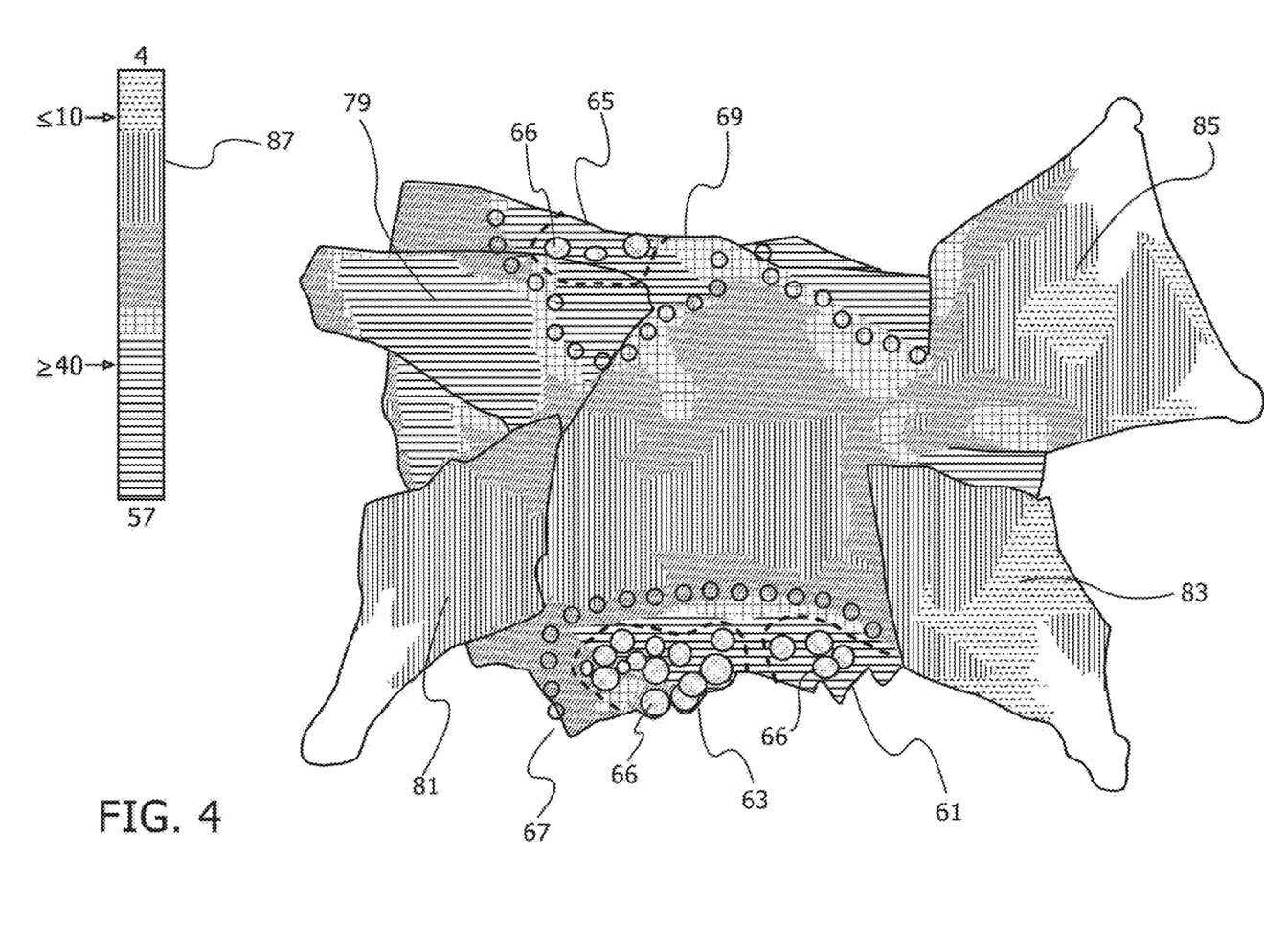
FIG. 4 is a functional electroanatomical map in the postero-anterior projection, showing CFAE's and ganglionated plexi, in accordance with a disclosed embodiment of the invention.
Figure 5:
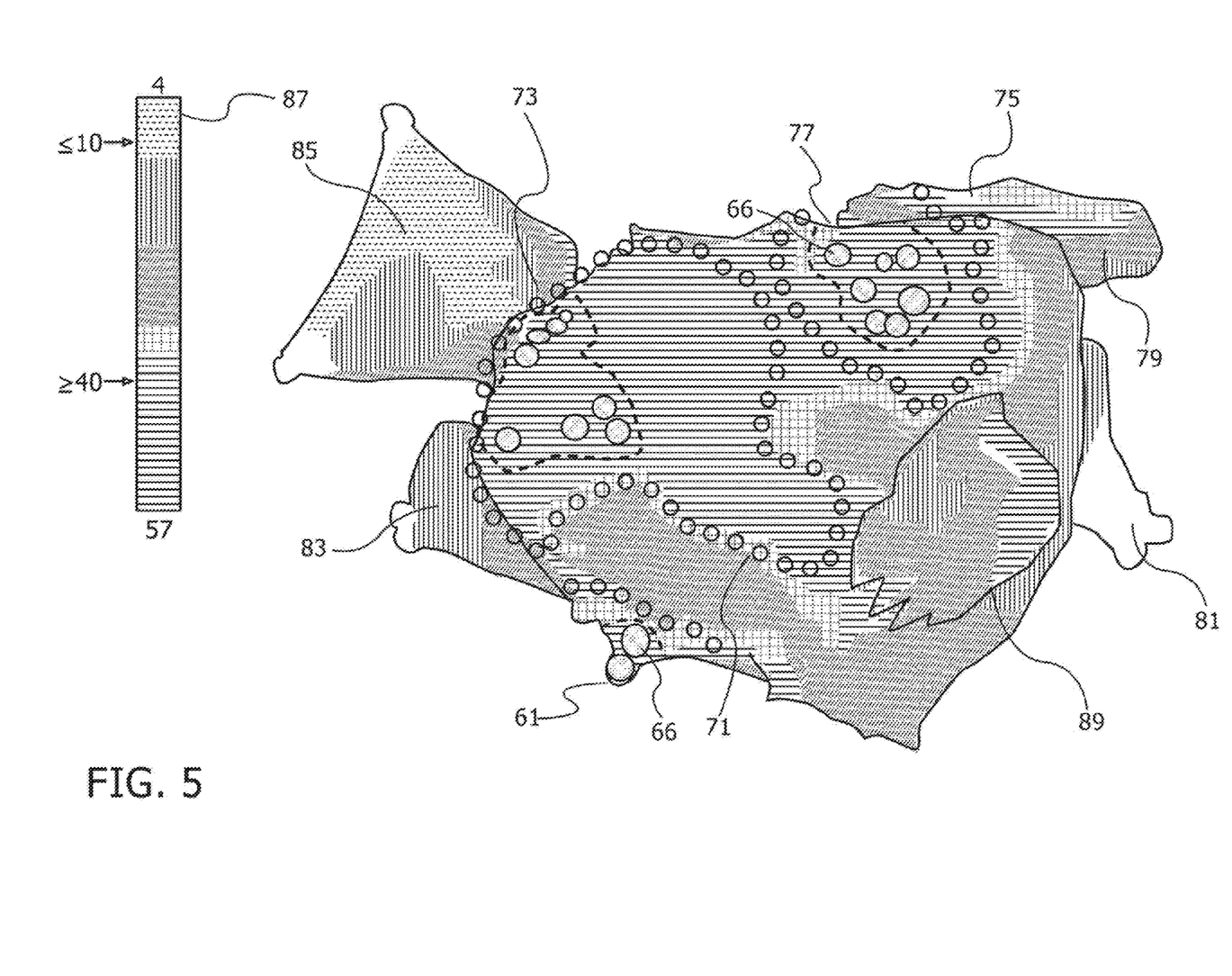
FIG. 5 is a functional electroanatomical map in the right anterior oblique projection, showing CFAE's and ganglionated plexi, in accordance with a disclosed embodiment of the invention.

Functional electro-anatomic maps may be generated, for example using the above-noted CARTO XP EP Navigation and Ablation System, to display the associations of ganglionated plexi and CFAE complexes on a functional electroanatomical map. Reference is now made to FIG. 4 and FIG. 5, which are functional electroanatomical maps in the postero-anterior and right anterior oblique projections, respectively, showing CFAE's and ganglionated plexi, in accordance with a disclosed embodiment of the invention. In FIG. 4 regions 61, 63, 65 typify areas containing ganglionated plexi (shown as circles 66), and are located within larger areas 67, 69, having relatively large number of CFAE's. The larger areas 67, 69 are demarcated by broken lines. Area 67 is an infero-posterior area having large numbers of CFAE's. Area 67 contains the inferior left and inferior right ganglionated plexi in region 63 and region 61, respectively. Area 69, in the superior left portion, has large numbers of CFAE's, and includes the superior left ganglionated plexi. In FIG. 5, area 71 is a large area in the anterior right portion, and includes the anterior right ganglionated plexi in region 73. Area 75, in the superior left portion of the atrium, includes region 77 in which the superior left ganglionated plexi are located. To assist with orientation, the following structures are shown: left superior pulmonary vein 79, left inferior pulmonary vein 81, right inferior pulmonary vein 83, and right superior pulmonary vein 85. The mitral annulus occupies area 89. A key 87 encodes the number of CFAE's in any given area.

Once the CFAE's and ganglionated plexi are located, ablative therapy may be performed if indicated.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for mapping abnormal electrical activity in a heart of a living subject, comprising the steps of:
   obtaining electrical signal data from respective locations of the heart in an area of interest;
   automatically analyzing the signal data to identify complex fractionated electrograms or complex fractionated electrogram segments therein;
   determining if the number of identified complex fractionated electrograms in the area of interest exceed a predetermined threshold for complex fractionated electrograms or if the number of complex fractionated electrogram segments in the area of interest achieve a maximal number;
   identifying one or more of the locations in the area of interest as having ganglionated plexi if the number of identified complex fractionated electrograms in the area of interest exceeded the predetermined threshold for complex fractionated electrograms or if the number of complex fractionated electrogram segments in the area of interest achieved the maximal number;
   deriving an electroanatomic map of the heart from the signal data that includes a spatial distribution of the complex fractionated electrograms and the ganglionated plexi, the electroanatomical map including a key encoding the number of complex fractionated electrograms in any area of interest; and
   displaying the spatial distribution of the complex fractionated electrograms and the ganglionated plexi with the key encoding the number of complex fractionated electrograms in any area of interest of the electroanatomic map.

2. The method according to claim 1, wherein identifying one or more of the locations comprises determining that a number of the complex fractionated electrograms at the one or more of the locations complies with a predefined criterion.

3. The method according to claim 2, wherein compliance with the predefined criterion comprises identifying ones of the locations wherein the complex fractionated electrograms exceed a threshold number.

4. The method according to claim 2, wherein compliance with the predefined criterion comprises identifying ones of the locations having locally maximal numbers of complex fractionated electrograms.

5. The method according to claim 1, further comprising the steps of:
   electrically stimulating a selected one of the locations that presumptively contain ganglionated plexi;
   recording responsively to the step of electrically stimulating a cardiovascular response comprising at least one of a reduction in sinus rate, a reduction in blood pressure, and a period of asystole; and
   thereafter reporting a confirmation of a presence of the ganglionated plexi in the selected one of the locations.

6. The method according to claim 1, wherein deriving an electroanatomic map comprises coding the electroanatomic map according to numbers of the complex fractionated electrograms detected in the respective locations.

7. An apparatus for mapping electrical activity in a heart of a living subject, comprising:
   a memory for storing electrical signal data from respective locations in an area of interest of the heart;
   a processor configured to access the memory and automatically analyze the signal data to identify complex fractionated electrograms or complex fractionated electrogram segments in the area of interest, and to determine when the number of identified complex fractionated electrograms in the area of interest exceed a predetermined threshold for complex fractionated electrograms or when the number of complex fractionated electrogram segments in the area of interest achieve a maximal number, and identify one or more of the area of interests as having ganglionated plexi when the number of identified complex fractionated electrograms in the area of interest exceeded the predetermined threshold for complex fractionated electrograms or when the number of complex fractionated electrogram segments in the area of interest achieved the maximal number;
   an electroanatomic map of the heart is derived from the signal data that includes a spatial distribution of the complex fractionated electrograms and the ganglionated plexi, the electroanatomical map including a key encoding the number of complex fractionated electrograms in any area of interest; and
   a display for presenting the electroanatomic map to an operator.

8. The apparatus according to claim 7, wherein the processor is operative to identify one or more of the locations by determining that a number of the complex fractionated electrograms at the one or more of the locations complies with a predefined criterion.

9. The apparatus according to claim 8, wherein compliance with the predefined criterion comprises an identification of ones of the locations wherein the complex fractionated electrograms exceed a threshold number.

10. The apparatus according to claim 8, wherein compliance with the predefined criterion comprises an identification of ones of the locations having locally maximal numbers of complex fractionated electrograms.

11. The apparatus according to claim 7, wherein the processor is operative to record responsively to an electrical stimulation of selected ones of the locations a cardiovascular response comprising at least one of a reduction in sinus rate, a reduction in blood pressure, and a period of asystole; and thereafter report a confirmation of a presence of the ganglionated plexi in the selected ones of the locations.

12. The apparatus according to claim 7, wherein the processor is operative to code the electroanatomic map according to numbers of the complex fractionated electrograms detected in the respective locations.

* * * * *